United States Patent [19]

Simbruner et al.

[11] Patent Number: 4,488,558

[45] Date of Patent: Dec. 18, 1984

[54] BIRTH MONITOR

[75] Inventors: Georg Simbruner; Rudolf Rudelstorfer, both of Vienna, Austria

[73] Assignee: Innova Wiener Innovationsgesellschaft m.b.H., Vienna, Austria

[21] Appl. No.: 388,740

[22] Filed: Jun. 15, 1982

[30] Foreign Application Priority Data

Jun. 16, 1981 [AT] Austria ................... 2678/81

[51] Int. Cl.³ ............................................. A61B 5/04
[52] U.S. Cl. ..................................... 128/642; 128/736
[58] Field of Search ................. 128/642, 736, 419 R, 128/784, 785, 786, 788, 741, 742, 303.1

[56] References Cited

U.S. PATENT DOCUMENTS

| | | | |
|---|---|---|---|
| 3,533,397 | 10/1970 | Scher | 128/742 |
| 3,827,428 | 10/1976 | Hon et al. | 128/642 |
| 4,090,504 | 5/1978 | Nathan | 128/670 |
| 4,141,365 | 2/1979 | Fischell et al. | 128/642 |
| 4,148,304 | 4/1979 | Mull | 128/736 |
| 4,180,080 | 12/1979 | Murphy | 128/642 |
| 4,190,058 | 2/1980 | Sagi | 128/736 |
| 4,217,910 | 8/1980 | Khalil | 128/670 |
| 4,246,784 | 1/1981 | Bowen | 128/736 |
| 4,297,685 | 10/1981 | Brainard | 128/736 |
| 4,299,232 | 11/1981 | Zilianti | 128/642 |
| 4,301,806 | 11/1981 | Helfer | 128/642 |
| 4,308,013 | 12/1981 | Major | 128/742 |
| 4,311,154 | 1/1982 | Sterzer et al. | 128/736 |

FOREIGN PATENT DOCUMENTS

| | | |
|---|---|---|
| 59701 | 2/1981 | European Pat. Off. |
| 39443 | 4/1981 | European Pat. Off. |
| 1087752 | 8/1960 | Fed. Rep. of Germany |
| 2619471 | 5/1976 | Fed. Rep. of Germany |
| 2749048 | 5/1979 | Fed. Rep. of Germany |
| 2930663 | 7/1979 | Fed. Rep. of Germany |
| 2913048 | 10/1980 | Fed. Rep. of Germany |
| 7518822 | 6/1975 | France |

OTHER PUBLICATIONS

"An Approach to Study of Brain Damage", Rosen et al., 1-1-73.
Medicinal and Biological Engineering, "A modified Internal Temperature Measurement Device", pp. 361-364, May 1976 /T. Yamazaki et al.
A Telemetry System For Fetal Intensive Care During Labor & Delivery, M. R. Neuman, 1970.

Primary Examiner—Lee S. Cohen
Assistant Examiner—Steven Falk
Attorney, Agent, or Firm—Karl F. Ross

[57] ABSTRACT

A system for monitoring the birth of a child, e.g. to allow immediate response to a blood circulation failure or metabolic distress symptom, comprises a support member on which is mounted an intrusive ekg measuring electrode and heat-flow detector. The heat-flow detector responds to the thermal flux at the head or other body portion of the infant and produces a signal which can be compared with a set point value.

13 Claims, 5 Drawing Figures

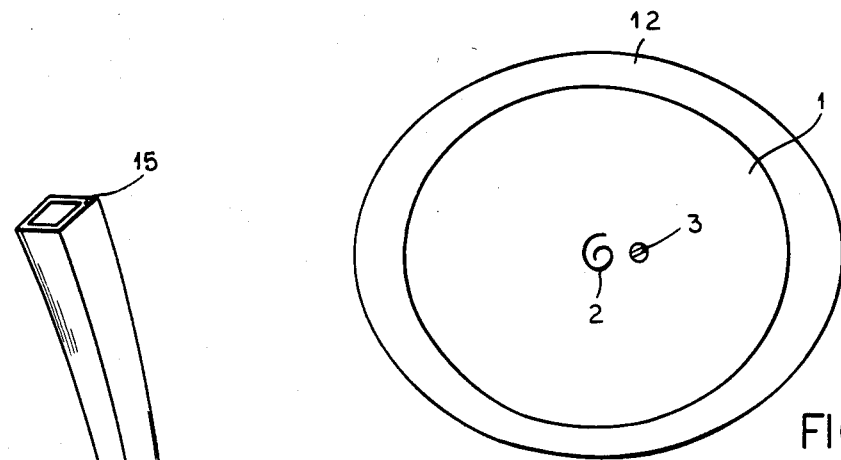
FIG.1
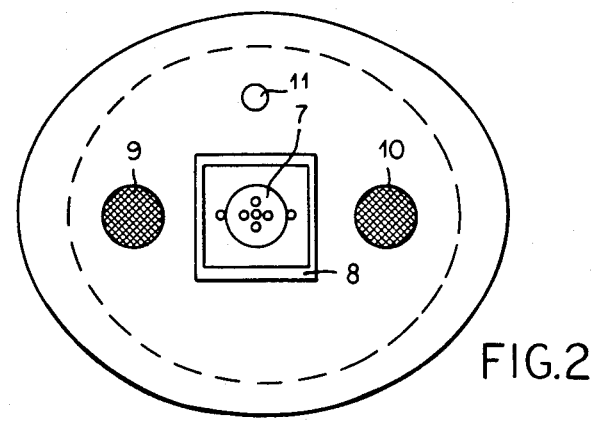
FIG.2
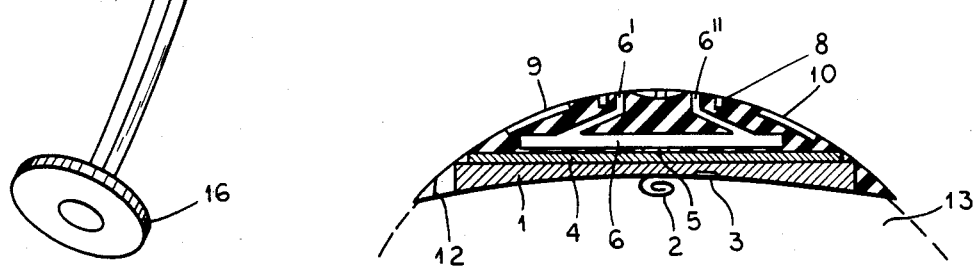
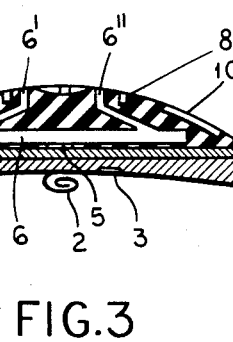
FIG.4    FIG.3
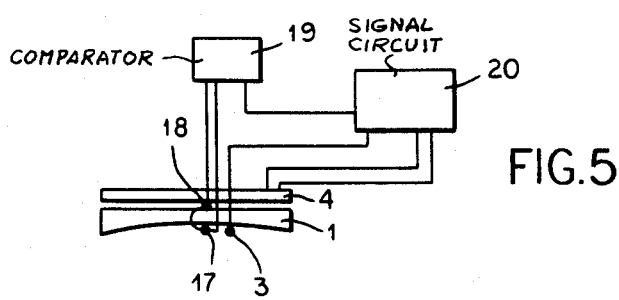
FIG.5

BIRTH MONITOR

FIELD OF THE INVENTION

Our present invention relates to a sensor forming part of a system for monitoring the birth of an infant and, more particularly, to a birth-monitoring system which includes a sensor which can be affixed to the leading portion of the fetus as it moves through the birth passage, this leading portion being generally the head.

BACKGROUND OF THE INVENTION

Sensors for monitoring the condition of a fetus, especially electrically conductive sensors of the intrusive or skin-penetrating type, have been proposed heretofore to enable the condition of the fetus to be monitored during the birth process, especially by monitoring the electrocardiagram of the fetus.

In general, the prior art electrodes for this purpose have not proved to be fully satisfactory because of a lack of reliability of the electrode, i.e. the sensor, the inability to diagnose adequately, from the data obtained, a developing or existing condition warranting immediate attention, and other reasons which derive from the means in which the sensor or electrode is applied.

Birth-monitoring systems of the conventional type can generally be considered in three categories. A first monitors the fetus electrocardiographically. A second measures extra-uterine and/or intra-uterine pressure fluctuations, especially the strength of labor contractions. The third analyzes the oxygen partial pressure or pH values of the blood, either by direct sampling of the fetal blood at the scalp of the fetus or by sensors which are fixed to the scalp.

All of these approaches have disadvantages, and a common disadvantage of all of them is that they are not fully capable of indicating danger to the fetus so that frequently, as a result of ambiguity in the measurements, the birth is concluded prematurely with the use of forceps and other instruments which may endanger the child or the mother. Sometimes, because of ambiguities in the results, a caesarean section is unnecessarily performed.

OBJECTS OF THE INVENTION

It is the principal object of the present invention to provide a birth-monitoring system which is more reliable and accurate than earlier monitoring systems and especially is capable of avoiding premature use of instruments or caesarean section.

Another object of this invention is to provide an improved sensor for a monitoring device or system which has a reduced tendency toward failure, provides a more significant measurement of the condition of the child or fetus, and which is comparatively simple.

SUMMARY OF THE INVENTION

These objects and others which will become apparent hereinafter are attained, in accordance with the present invention, with a monitoring system including at least one sensor which can be affixed to the body of the fetus, e.g. the head of the fetus or a leading portion of the fetus in the birth process, this sensor comprising a support member carrying at least one intrusive electrocardiagram (ekg) electrode and additionally provided, in accordance with the invention, with a thermal-flow detector which monitors the heat flow of the body portion to which the sensor is affixed.

According to the invention, the heat flow detector comprises a heat flow plate adapted to lie adjacent the skin of the fetus or child and juxtaposed on its opposite sides with a pair of thermoelements which can be affixed to this plate, the thermoelements connected to appropriate circuitry being adapted to measure the heat flow at the skin of the fetus with which the sensor is in contact.

The thermoelements can include a thermistor disposed in the intrusive electrode or directly adjacent the latter for measuring the tempararture of the skin of the child or fetus and whose output signal, through an appropriate circuit, is recorded, displayed or indicated.

The sensor of the present invention has a number of advantages which will be more fully appreciated as the function of the sensor is developed below.

Firstly, it should be noted, the sensor of the present invention has a conventional measuring device, e.g. the intrusive electrode, for the fetal ekg and can be used for the conventional pressure measurements, e.g. the intrauterine pressure measurements through still another sensor.

In addition, the sensor of the invention has the thermal-flow sensor which allows the material exchange and blood circulation of the head and especially the brain to be monitored during the course of the birth and while the new-born infant is in the birth passage.

The monitoring is thus effective in an intra-uterine and in an extra-uterine manner so that a more effective warning of any distress can be obtained.

As long as there is a normal material exchange (blood oxygen/carbon dioxide exchange) and circulation in the head and especially the brain, the rate of flow of heat from the head to the ambient region is substantially constant and indeed is an ascertainable rate which does not fluctuate significantly. Should the blood supply to the head and the brain be affected in a manner tending to decrease this supply, even if, as is usually the case, the material exchange is unaffected for a relatively long period thereafter, there is a significant increase in the heat transferred from the head because the heat generated by metabolism as a result of this material exchange in the head is not carried away by the circulating blood.

For a postpartum infant with a hypoplastic left heart, i.e. a sharply reduced circulation, the material exchange and the metabolism can be increased by prostaglandins. This results in an increase in the heat flow from the head of the postpartum infant because it is not possible to increase the circulation in such cases to overcome the increased heat generated.

In a healthy postpartum infant to whom Alupent is administered, there is also an increase in the material exchange or metabolism with increase in heat flow from the head without significant increase in blood circulation.

An increase in heat flow from the head can thus be observed when less heat is being carried away by the circulation (indicating a paucity of circulation) or when artificial means create an increase in metabolism or material exchange. The latter phenomenon generally is a result of inappropriate medication or overmedication.

It is thus apparent that the system of the invention allows a number of disorders which could not be ascertained heretofore to be monitored in the infant during the birth proper so that the attending physician can be signalled when, during the birth process, a distress symptom occurs, e.g. in terms of reduction in heat dissipation or an excess of heat dissipation from the head. The changes can also be correlated with heartbeat or frequency as ascertained by the ekg monitor.

BRIEF DESCRIPTION OF THE DRAWING

The above and other objects, features and advantages of the present invention will become more readily apparent from the following description, reference being made to the accompanying drawing in which:

FIG. 1 is an elevational view of the surface of a sensor from its skin-contacting side according to the invention;

FIG. 2 is an elevational view of the side of the sensor turned away from the skin;

FIG. 3 is a central transverse section through the sensor;

FIG. 4 is a perspective view of a tube for introducing the sensor; and

FIG. 5 is a diagram, primarily in block form, showing the principles of the invention.

SPECIFIC DESCRIPTION

FIG. 1 shows the side of a sensor according to the invention adapted to be applied to the body of the infant or fetus, e.g. to the head of the fetus. This side of the sensor is formed primarily by a disk-shaped support member 12, the largest portion of the area of which, turned toward the infant, is constituted by a heat-flow detector 1.

In the middle of the latter and insulated from the conductive metal of the plate 1, is an intrusion electrode 2 adapted to pierce the skin of the scalp.

To this end, the electrode 2, which is constituted by a conical spiral of conductive wire, can be caused to pierce the skin of the scalp by rotation of the body 12. The electrode 2, which can be utilized to register the ekg of the child thus can also be used to detect the heartbeat or pulsebeat frequency.

The sensor, while preferably applied to the head of the infant emerging from the uterus, can also be applied to any leading portion of the body during the descent through the birth passage, as long as the plate 1 is in surface contact with the skin and the intrusion electrode pierces the latter. Consequently, when reference is made herein to the head of the infant, it should be understood to include other portions of the body to which the sensor may be applied as well.

Within the intrusion electrode 2 or directly adjacent the latter and in contact with the skin, a temperature measuring device such as the thermistor 3 is provided for direct measurement of the skin temperature.

From FIG. 3 it may be seen that the support body 12 and the plate 1 can be concave toward the side at which it engages the infant, preferably with a curvature substantially conforming to the curvature of the scalp of the infant or other body portions to be engaged by the sensor, thereby ensuring maximum surface contact between the skin and the plate 1.

The outer surface of the sensor may be convex and can have a radius of about 1.5 centimeters and a height (thickness) of 4 to 6 millimeters. The diameter of the sensor can be about 30 mm.

The concave side of the body 12 is provided with the heat-flow detector in the middle of which is provided the intrusion electrode 2 for registering heartbeat frequency, in the manner described, and for affixing the sensor by implantation.

Above the plate 1, a heat foil or plate 4 is provided and below this there is a further thermistor 5 which is disposed in the region of the center of the body 12.

The heat-flow sensor itself comprises a pair of thermoelements (see FIG. 5), represented at 17 and 18 and disposed opposite one another across the conductive plate 1, forming the heat-flow detector with these thermoelements.

The thermoelement can be thermocouples with fusion beads or junctions such that the junction of the thermoelement 17 is in contact with the skin, while the junction of the thermoelement 18 is in contact with the opposite side of the plate 1 and/or the heating device 4.

The temperature differential across the two thermoelements 17 and 18 thus is a measure of the heat flow from the head of the infant to the body 12 and the environment.

As noted, the plate 1 is a concave member whose temperature on opposite sides is measured by the thermoelements 17 and 18 and which can deliver the heat-flow signal to a comparator 19.

The comparator 19 ascertains any difference between the measured heat flow and a set point value of the heat flow which is recognized to correspond to a normal value for the part of the body to which the sensor is affixed. Any deviation is delivered to a circuit 20 which can be a threshold circuit and serve to signal a distress condition in the infant, should one arise.

The circuit 20 can also be provided with means for passing an electric current through the heating plate 4 so that the system of the invention can operate substantially in a zero heat flux technique.

In this system, the plate 4 is heated to a temperature which is the same as the scalp/skin or brain temperature of the infant. Thus, under normal conditions, the temperature on both sides of the plate 1 may be the same. A temperature differential will then be detected only in the event of an abnormal condition.

For example, a positive temperature differential can signal a greater heat development than the normal development, while the negative temperature differential will signal a diminished heat flow so that corrective action can be taken. The thermistor 3 can provide the input for controlling the temperature of the plate 4 based upon a deep brain temperature or deep internal body temperature. Alternatively, the heat-flow detector 1, 17, 18 can control the heating of foil or plate 4 through the comparator 19 and the control/indicator/recording circuit 20 so that the heat supplied balances the heat lost from the skin. The internal brain or body temperature can then be measured by the thermistor 3 to provide the monitored signal.

In some cases it is advantageous to increase the heat flow from the body of the infant and in such cases a cooling chamber can be provided in the sensor as shown at 6, passages 6' and 6" being provided to circulate a coolant through this chamber.

The lower the temperature of this coolant or the parts of the body 12 in contact therewith, the greater will be the temperature differential measured by the sensor and the greater will be the heat transfer from the skin surface.

A greater temperature differential, e.g. of several degrees centigrade, can be more accurately measured than a smaller temperature differential, thereby increasing the accuracy of the diagnosis.

Instead of a circulating coolant, the cooling means can be formed by a semiconductor element, e.g. a thermopile, operating with the Peltier effect and to which an electric current is supplied. The thermistor 5 can measure the reduced temperature generated by the cooling means. The convex side of the body 12 is provided with a cable connector 7 for connecting the various electric currents supplied, ducts and like electrical conductors, and the passages for the cooling fluid if provided.

The connector 7 is surrounded by a square channel 8 which can receive the end 15 of a guide tube 14 which is a highly flexible, square cross-section tube having a length of about 25 centimeters (see FIG. 4). The tube can have a diameter or a diagonal dimension of about 1.0 centimeters and a circular cross section, apart from the square end, can have a radius of 0.5 centimeters. It can be composed of a synthetic resin material which is not toxic to the body and has longitudinal stiffness, e.g. polyethylene. The end 15 fits into the channel 8.

The other end of the guide tube 14 is provided with a wheel-shaped rotating device 16 for rotating the tube 14 about its longitudinal axis whereby the sensor can be passed with the tube into and through the birth passage and the electrode 2 implanted by rotation of the body 12. The interior of the tube 14 carries the cable and tubes running to the circuitry 19, 20 and to the means for circulating the coolant.

Along the periphery of the side of the body 12 turned away from the infant, a disk-shaped metal plate 9 forming an indifferent electrode is provided (FIG. 2) for measuring the heart frequency of the child in combination with the electrode 2.

A further thermistor 10 can be provided opposite the electrode 9 for measurement of the environment temperature, i.e. the temperature of the mother, while an opening 11 is provided for a pressure measurement tube adapted to respond to intra-uterine pressure. The intra-uterine pressure measurement can be used as a correcting signal for the heat flow value. The body 12 in which the above-described elements are encapsulated, can be composed of a body-compatible, watertight, electrically-insulating and sterilizable material such as a silicone rubber.

The circuitry for recording and displaying the ekg, the pulse rate, the intra-uterine and/or extrauterine pressure and the various temperatures are conventional in the art and have not been illustrated.

We claim:

1. In a system for monitoring the birth of an infant which comprises a sensor provided with at least one intrusion electrode adapted to be affixed to a portion of the body of an infant during parturition and providing an ekg output, said sensor including a support member having a first side carrying said intrusion electrode and adapted to lie against the skin of said infant and a second side opposite thereto, the improvement which comprises a heat-flow detector on said member, responsive to the heat flow from the skin of the infant for generating an output signal at least upon a deviation of said heat flow from a normal value, and means responsive to said detector for signaling such deviation, said detector comprising a heat-flow plate formed on the first side of said member and engageable with said infant, a pair of thermoelements disposed on opposite sides of said plate, and means for creating a thermal condition at least on a side of said plate turned away from the infant whereby a temperature differential detector between said thermoelements represents said heat flow from the skin of the infant.

2. The improvement defined in claim 1 wherein said electrode is mounted on but insulated from said plate, said plate carrying a thermistor forming one of said thermoelements at least in the immediate vicinity of said electrode for measuring the temperature of the skin of the infant, said thermistor being connected to a circuit for indicating the skin temperature measurement of said thermistor and constituting said means responsive to said detector.

3. The improvement defined in claim 1 wherein said means for creating a thermal condition comprises a heating element lying along a face of said plate turned away from said infant.

4. The improvement defined in claim 3, further comprising control means responsive to the output of said detector for controlling the heating of said heating element.

5. The improvement defined in claim 4 wherein said means responsive to said detector includes a comparator circuit receiving an output signal from said detector and comparing it to a predetermined set point signal, a thermistor at least adjacent said electrode, and evaluating means connected to said comparator circuit for enabling the display or registration of a temperature signal measured by said thermistor and representing brain or body internal temperature.

6. The improvement defined in claim 1 wherein said means for creating a thermal condition is cooling means along the side of said plate turned away from said infant.

7. The improvement defined in claim 6 wherein one of said thermoelements is a temperature measuring thermistor in said member between said cooling means and said plate.

8. The improvement defined in claim 1 wherein said member is formed on said second side with an indifferent electrode for registering heartbeat frequency.

9. The improvement defined in claim 1 wherein said member is formed on said second side with a thermistor for measuring ambient temperature.

10. The improvement defined in claim 1 wherein said member is formed with a cable connector electrically connected to said electrode, and a square channel surrounding said connector on said second side of said member the improvement further comprising a guide tube having an end received in said channel for passing said sensor through the birth passage, said tube enabling the passage of said cable connector therethrough.

11. The improvement defined in claim 1 wherein said first side of said member is concave, said second side of said member is convex, the diameter of said member is about 30 millimeters and the thickness of said sensor is about 4 to 6 millimeters.

12. The improvement defined in claim 1 wherein substantially the entire surface of the side of said sensor adapted to lie against the skin of said infant is formed by said detector and said detector is concave toward the infant.

13. The improvement defined in claim 1 wherein the means responsive to said detector is adapted to indicate and record the output from said detector and electrode separately.

* * * * *